US012800559B2

(12) United States Patent
Alrasheed et al.

(10) Patent No.: US 12,800,559 B2
(45) Date of Patent: Nov. 17, 2026

(54) PREDICTION OF THE WAX APPEARANCE TEMPERATURE BY CORRELATION WITH CRUDE OIL BIOMARKERS

(71) Applicant: SAUDI ARABIAN OIL COMPANY, Dhahran (SA)

(72) Inventors: Faisal Alrasheed, Dammam (SA); Egbukole Okechukwu, Dhahran (SA); Muqbil Alkhalaf, Dhahran (SA); Tao Chen, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 288 days.

(21) Appl. No.: 18/664,675

(22) Filed: May 15, 2024

(65) Prior Publication Data

US 2025/0354966 A1 Nov. 20, 2025

(51) Int. Cl.
*G01N 30/86* (2006.01)
*G01N 30/72* (2006.01)
(Continued)

(52) U.S. Cl.
CPC ..... *G01N 30/8631* (2013.01); *G01N 30/7206* (2013.01); *G01N 33/2823* (2013.01); *E21B 37/06* (2013.01); *G01N 2030/025* (2013.01)

(58) Field of Classification Search
CPC ........... G01N 30/8631; G01N 30/7206; G01N 33/2823; G01N 2030/025; G01N 30/72;
(Continued)

(56) References Cited

U.S. PATENT DOCUMENTS

| | | | |
|---|---|---|---|
| 6,841,779 | B1 | 1/2005 | Roehner et al. |
| 11,022,588 | B2 | 6/2021 | Koseoglu et al. |

(Continued)

FOREIGN PATENT DOCUMENTS

| | | | |
|---|---|---|---|
| GB | 2300272 | B | 5/1998 |
| WO | 93/23547 | A1 | 11/1993 |

(Continued)

OTHER PUBLICATIONS

Siddhartha Seth, et al, “Diachronic viscosity increase in waxy crude oils,” Journal of Petroleum Science and Engineering, 2004 (11 pages).

(Continued)

*Primary Examiner* — Ellen M McAvoy
(74) *Attorney, Agent, or Firm* — Osha Bergman Watanabe & Burton LLP

(57) ABSTRACT

A method to predict a wax appearance temperature of crude oil includes injecting a sample of crude oil into a chromatography instrument, measuring a plurality of peak areas using the chromatography instrument, determining a composite measurement from the plurality of peak areas, and determining the wax appearance temperature by a correlation of the composite measurement with the wax appearance temperature. A wellbore operation includes determining a wax appearance temperature, comparing the wax appearance temperature to an operating temperature of the wellbore, and forecasting a need for a mitigation program.

15 Claims, 6 Drawing Sheets

(51) Int. Cl.

| | |
|---|---|
| ***G01N 33/28*** | (2006.01) |
| *E21B 37/06* | (2006.01) |
| *G01N 30/02* | (2006.01) |

(58) Field of Classification Search

CPC ........... G01N 30/8634; G01N 30/8637; G01N 30/88; G01N 2030/8854; E21B 37/06

See application file for complete search history.

(56) References Cited

U.S. PATENT DOCUMENTS

| | | | | |
|---|---|---|---|---|
| 2008/0141767 | A1* | 6/2008 | Raghuraman ...... | G01N 33/2823 73/152.55 |
| 2011/0288788 | A1 | 11/2011 | Oh | |
| 2012/0053838 | A1* | 3/2012 | Andrews ................. | E21B 49/10 73/23.35 |
| 2015/0106028 | A1 | 4/2015 | Koseoglu et al. | |
| 2016/0097717 | A1 | 4/2016 | Yuen et al. | |
| 2016/0363533 | A1* | 12/2016 | Koseoglu ............... | G01N 21/64 |
| 2019/0017377 | A1* | 1/2019 | He ..................... | G01N 33/2823 |
| 2020/0033317 | A1* | 1/2020 | Patel ...................... | G01N 33/28 |
| 2021/0024849 | A1 | 1/2021 | Tagawa et al. | |
| 2023/0228721 | A1* | 7/2023 | Atwah ................. | G01N 33/241 73/23.37 |
| 2025/0067719 | A1* | 2/2025 | Rowe ..................... | B01D 29/52 |

FOREIGN PATENT DOCUMENTS

| | | | |
|---|---|---|---|
| WO | 2015041672 | A1 | 3/2015 |
| WO | 2018187898 | A1 | 10/2018 |

OTHER PUBLICATIONS

Andre Aguiar, et al., "Application of comprehensive two-dimensional gas chromatography coupled to time-of-flight mass spectrometry to biomarker characterization in Brazilian oils," Fuel, 2010 (9 pages).

Tao Zhu, et al., "Evaluation of Wax Deposition and Its Control During Production of Alaska North Slope Oils," Oil & Natural Gas Technology, 2008 (296 pages).

Arya Hosseinipour, et al., "Calculation of wax appearance temperature directly from hydrocarbon compositions of crude oil," International Journal of Advanced and Applied Sciences, 2019 (5 pages).

* cited by examiner

PREDICTION OF THE WAX APPEARANCE TEMPERATURE BY CORRELATION WITH CRUDE OIL BIOMARKERS

BACKGROUND

Wax is defined as a hydrocarbon comprised primarily of paraffin with a carbon number ranging from C17 to C60. Wax deposition is one of the flow assurance challenges in the oil and gas industry that impacts flow which results in production loss, equipment damage or shutdown. Wax appearance temperature (WAT) is an important operational parameter that is determined in order to assess the wax precipitation tendency. The WAT may help in determining chemical treatments and remedies, reasons of fouling, supports corrective action, determines scraping frequency, evaluates wax inhibitors and design optimization.

Wax thermal analysis including determination of the WAT is an important operational parameter that is determined in order to assess the wax precipitation tendency and plan for mitigation. As cooling of the extracted wax continues, the paraffin's form a solid crystalline wax structure. The crystal growth produces wax aggregation, which reaches a point where it precipitates out of the crude oil. During the cooling process, the solvating power of the oil matrix decreases resulting in precipitation of the wax solid particles. Accordingly, there exists a need for rapid determination of the WAT in order to prevent production loss, equipment damage, and shutdown.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method to predict a wax appearance temperature of crude oil. The method may include injecting a sample of crude oil into a chromatography instrument. The method may include measuring a plurality of peak areas using the chromatography instrument. The method may further include determining a composite measurement from the plurality of peak areas and determining the wax appearance temperature by a correlation of the composite measurement with the wax appearance temperature.

In another aspect, embodiments disclosed herein relate to a wellbore operation. The wellbore operation may include determining a wax appearance temperature. The wellbore operation may include comparing the wax appearance temperature to an operating temperature of the wellbore. The wellbore operation may further include forecasting a need for a mitigation program.

Other aspects and advantages of the claimed subject matter will be apparent from the following description and the appended claims.

DETAILED DESCRIPTION

Embodiments herein generally relate to methods of predicting a wax appearance temperature in crude oil and forecasting if a mitigation program is needed in a wellbore operation. The wax appearance temperature (WAT) is a measurement that indicates the tendency for wax to form in a wellbore operation. Waxes may be defined as paraffins of a carbon length between 17 and 60 carbons. If the wellbore is operating at a temperature lower than the WAT, wax may form. Waxes may cause flow assurance problems, as well as plug filters, damage equipment, and may lead to a wellbore operation shutting down. The WAT may indicate a wax precipitation tendency based on the operating temperature of the wellbore. A mitigation program may be needed to prevent flow assurance problems. The mitigation program may be thermal or chemical. For the purposes of this disclosure, wax appearance temperature may also refer to the cloud point.

In one aspect, embodiments disclosed herein relate to a method for predicting a wax appearance temperature of crude oil. The method in accordance with the present disclosure includes a chromatography instrument. The chromatography instrument may be a gas chromatography instrument connected with a mass spectroscopy instrument. In some embodiments, a plurality of peak areas is determined from the chromatography instrument. The plurality of peak areas may correspond to a plurality of biomarkers. The plurality of biomarkers may correspond to specific carbon compounds present in the crude oil. The plurality of peak areas may result in a composite measurement. The composite measurement may linearly correlate to the wax appearance temperature.

Chromatography is a useful technique for separation of the components in a mixture. Chromatographic separation is based on the affinity of the components in a mixture between a stationary phase and a mobile phase. The resulting separated components may be analyzed via a variety of methods to determine the identity of the components, the structure of the components, and the concentration of the components. The present disclosure is directed towards using chromatography to separate a plurality of biomarkers from a sample of crude oil. The sample of crude oil may contain a mixture of carbon compounds.

Figure 1:
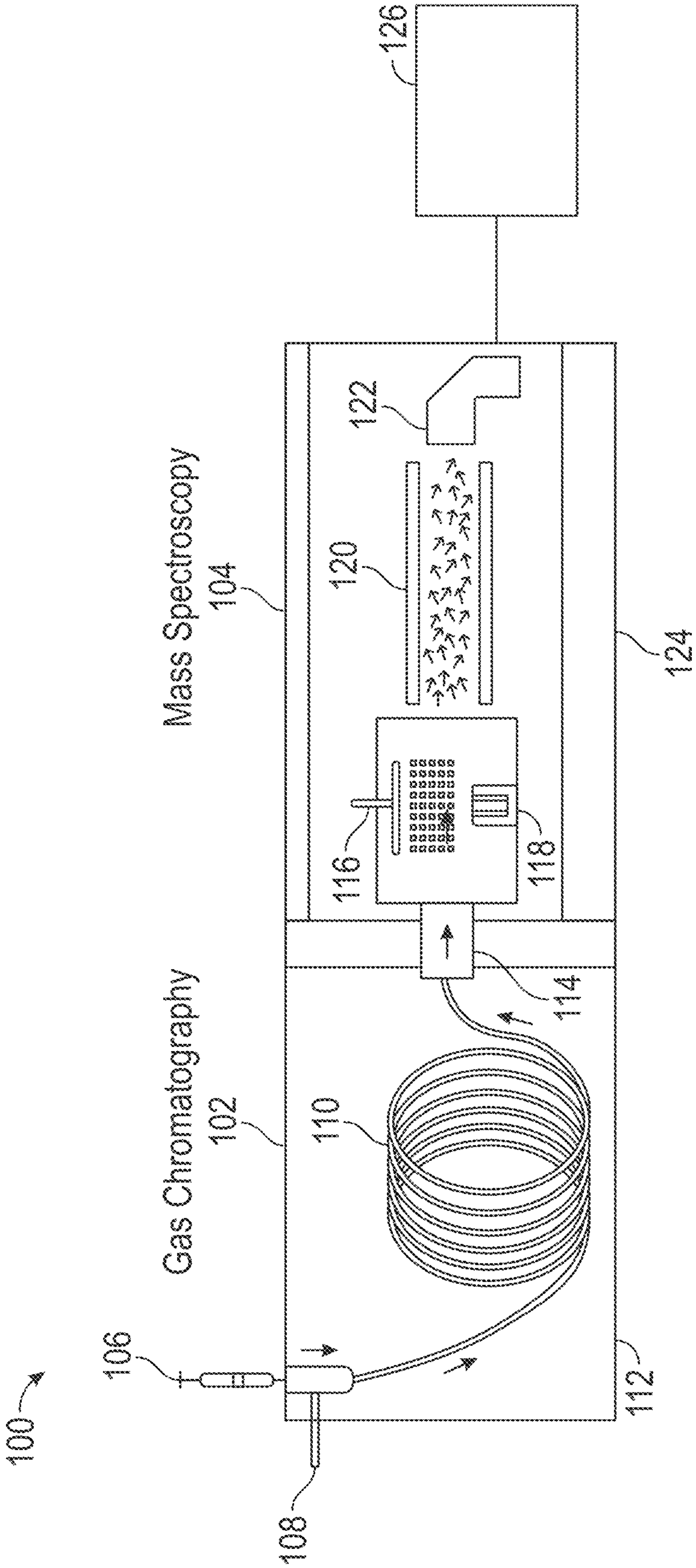
FIG. 1 is a schematic diagram of a chromatography instrument, according to one or more embodiments.

FIG. 1 is a schematic diagram of a chromatography instrument 100. The chromatography instrument 100 may include any instrument that is used for the separation of components in a mixture. The chromatography instrument 100 may include a gas chromatography instrument, a liquid chromatography instrument, a capillary electrophoresis instrument, a supercritical fluid chromatography instrument, and combinations thereof. In one or more embodiments, the chromatography instrument 100 is a gas chromatography instrument 102.

Chromatographic instruments are known to be hyphenated instruments to those of ordinary skill in the art. For the purposes of this disclosure, a hyphenated instrument is an instrument that is two or more instruments operated together that produce analytical results superior to the results of the individual instruments. The hyphenated instrument may include two instruments. A first instrument may be a gas chromatography instrument, a liquid chromatography instrument, a capillary electrophoresis instrument, a supercritical fluid chromatography instrument, and combinations thereof. A second instrument, according to one or more embodiments, may include a mass spectroscopy instrument, a flame-ionized detection instrument, and combinations thereof. The first instrument and second instrument may be operated together in any fashion, such that any first instrument may be operated with any second instrument. In one or more embodiments, the chromatography instrument 100 is a gas chromatography instrument 102 with a mass spectroscopy instrument 104.

As depicted in FIG. 1, the gas chromatography instrument 102 has an injection port 106. The injection port 106 may be connected to an automated injection system. The automated injection system may include an autosampler. In other embodiments, the injection port 106 may allow for manual injection.

In one or more embodiments, the gas chromatography instrument 102 includes a carrier gas inlet 108. The carrier gas inlet 108 is the inlet for a carrier gas. The carrier gas is considered the mobile phase of gas chromatography instruments. The carrier gas may include an inert gas. The inert gas may be helium gas, nitrogen gas, hydrogen gas, and combinations thereof.

The gas chromatography instrument 102 may include a column 110, in accordance with one or more embodiments. The column is considered the stationary phase of gas chromatography instruments. The column 110 may be any chromatographic column that provides sufficient separation. Sufficient separation is determined from column variables such as length, internal diameter, film thickness, and combinations thereof. A non-limiting example of the column 110 is a non-polar chromatographic column DB1 with a length of 60 meters, internal diameter of 0.25 millimeters, and a film thickness of 2.5 microns. Another non-limiting example includes non-polar chromatographic column DB-5.

In one or more embodiments, the column 110 may be enclosed in an oven 112. The column 110 may be heated in the oven 112. The oven 112 may be any temperature of a range of 25 to 430 °C. The temperature range may be extended from both ends of the range using customized settings. The temperature range may be lowered using cryogenic liquids. The temperature range may be increased using high temperature gas chromatography instruments equipped with a high temperature column or other suitable customization.

A transfer line 114 may connect the gas chromatography instrument 102 to the mass spectroscopy instrument 104, in accordance with one or more embodiments. The mass spectroscopy instrument 104 may include an ion source 116 and a filament 118. The ion source 116 may include sources of ions that are chemicals, electrons, or combinations thereof.

In one or more embodiments, the mass spectroscopy instrument 104 may include a mass analyzer 120. The mass analyzer 120 may be a quadrupole mass analyzer, an ion trap mass analyzer, a time-of-flight mass analyzer, a magnetic sector analyzer, an electrostatic mass analyzer, a quadrupole ion trap mass analyzer, an ion cyclotron resonance mass analyzer, and combinations thereof. In other embodiments, the mass spectroscopy instrument 104 may include a detector 122. The detector 122 may be an electron multiplier, a faraday cup, an array transducer, and combinations thereof. The mass spectroscopy instrument 104 may be enclosed in a vacuum system 124. The mass spectroscopy instrument 104 may be connected to a computer 126.

According to one or more embodiments, samples are injected into the injection port 106 of the gas chromatography instrument 102. The injection may use a chromatography syringe. The injection may be manual or through an automated injection system. The injection may be of a volume in the range of about 0.5 to about 5 μL. The injection may be split or split-less. The split injection may occur at a ratio in a range that may be chosen based on the instrument capability. For example, the split injection may occur at a ratio of from 1:1 to 1:500, for example 1:1, or 1:100, or 1:500. The injection may require less than five milliliters of organic solvents to rinse the chromatography syringe. Organic solvents may include acetone, hexanes, toluene, and a combination thereof.

In one or more embodiments, the carrier gas enters the gas chromatography instrument 102 through the carrier gas inlet 108. The carrier gas may have a flow rate. The flow rate may range from 1 to 2 milliliters per minute (mL/min).

According to one or more embodiments, injected samples are vaporized and mixed with the carrier gas that travels to the column 110. The components of the sample partition between the carrier gas of the mobile phase and the column of the stationary phase, where time, temperature, polarity, and boiling point control the separation. The temperature of the column 110 is controlled by the oven 112. The oven 112 may be at a static temperature or the temperature may be varied. In accordance with one or more embodiments, a temperature ramping program may be used. The temperature ramping program may increase the temperature of the oven 112 and the column 110 an amount of temperature over a period of time. The ramping program may include a rate of about 1 °C/min to 120 °C/min, where the ramping rate may be lower or higher, depending on the gas chromatography instrument capability.

The gas chromatography instrument 102 may produce separated samples. The separated samples may travel from the column 110 to the mass spectroscopy instrument 104 through the transfer line 114. The separated samples may be ionized by the ion source 116 and a filament 118 to produce ions. The ions may be produced from chemical ionization, electron ionization, and combinations thereof. The ions may be sorted by a mass analyzer 120. The mass analyzer 120 may be a quadrupole. The mass analyzer 120 may sort the ions over an increasing mass-to-charge (m/z) ratio. The m/z ratio may range from 1 to a maximum dependent on instrument capability. For example, a suitable mass spectroscopy instrument may detect up to about 2000 m/z.

The mass analyzer 120 may sort the ions based upon a mode selected for the mass spectroscopy instrument 104. Suitable modes include one or more of full scan monitoring, selected ion monitoring, multiple reaction monitoring, selected reaction monitoring, and scanning mode.

In one or more embodiments, full scan and selected ion monitoring are the modes used. For example, the mass spectroscopy instrument may be first run at full scan monitoring mode. Then, selected ion monitoring mode may be used to measure the peak area or heights of ions of interest. For example, the ions may be sorted by the quadrupole as follows: a crude oil sample separated by the column 110 reaches the ion source 116 of the mass spectroscopy instrument 104. The crude oil sample is exposed to a high energy electron beam from the filament 118. The high energy electron beam may have an energy of about 70 electron volts (eV). The outcome of the high energy electron beam is the ionization and fragmentation of the crude oil sample. The energy of the high energy electron beam may be varied depending on the amount of fragmentation desired. The resulting fragment ions are directed into the mass analyzer 120. The mass analyzer 120 may be a quadrupole. The mass analyzer 120 resolves the fragmented ions on the basis of their mass to charge ratios (m/z). Full scan monitoring involves scanning the mass range beginning at the smallest mass of fragmented ions to the highest mass expected for the fragmented ions. Selected ion monitoring helps in quantitative studies on the specific ions of interest in the spectra of compound(s) of interest.

According to one or more embodiments, the ions are detected by the detector 122. The detector 122 may convert the number of ions in the sample to an electrical signal. The electrical signal may be converted to data that is displayed on a computer 126. The data may include a chromatograph, retention times, m/z ratios, mass spectroscopy fragment patterns, peak areas, and combinations thereof.

Figure 2:
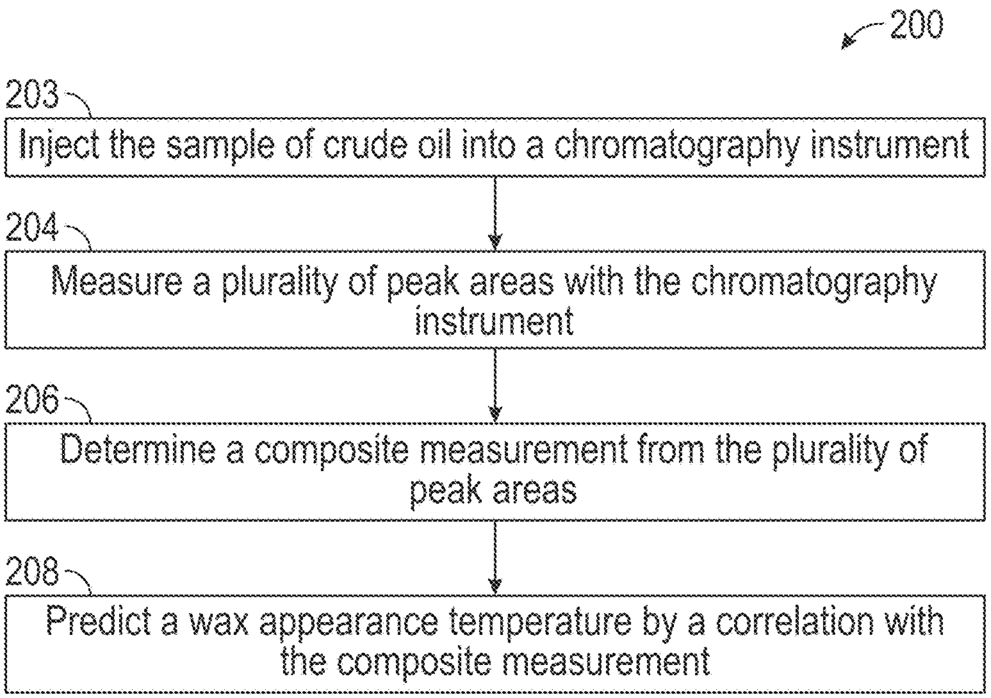
FIG. 2 is a flowchart of a method, according to one or more embodiments.

The present disclosure is directed towards predicting a wax appearance temperature. A method 200 for predicting a wax appearance temperature, in accordance with one or more embodiments, is depicted in FIG. 2. Initially, at block 203, the method 200 includes injecting a small volume of a sample of crude oil, where a sufficient volume for injection is obtained. For example, the small volume may be at least 0.5 milliliters. The sample of crude oil may be undiluted, such that dilution may not be needed. Method 200 does not depend on the origin of the sample of crude oil. For example, the sample of crude oil may be obtained from pipelines, wellbores, downhole, tanks, and any upstream, midstream, or downstream process or storage.

At block 203, method 200 includes injecting the sample of crude oil into a gas chromatography instrument 102 with a mass spectroscopy instrument 104, according to one or more embodiments. The injection may be direct by an operator or by an automated injection system. The automated injection system may be an autosampler. The injection may be split or splitless in a range that may be chosen based on the instrument capability. For example, the split injection may occur at a ratio of from 1:10 to 1:500, for example 1;1, or 1:100, or 1:500.

At block 204, method 200 includes measuring a plurality of peak areas with a chromatography instrument 100, in accordance with one or more embodiments. Measuring the plurality of peak areas may include separating the mixture of hydrocarbons in a sample of crude oil using a gas chromatography instrument 102 with a mass spectroscopy instrument 104. Measuring the plurality of peak areas may occur after injecting the sample of crude oil into the gas chromatography instrument, as in block 203. Once injected, block 204 may include separating the mixture of hydrocarbons in the sample of crude oil. Once separated, block 204 may include converting the separated mixture into ions. Block 204 may then include sorting the ions based on their respective m/z ratios. Once sorted, block 204 may include converting the ions into data that is displayed on the computer 126.

Method 200 according to one or more embodiments at block 204 includes analyzing the data from the gas chromatography instrument 102 with the mass spectroscopy instrument 104. The data may include a chromatograph. Analyzing the data from the chromatograph may include analyzing peaks that correspond to the concentration of m/z ratios found in the mixture of carbon compounds in the sample of crude oil. Measuring the plurality of peak areas as in block 204 may include integrating the area under the curve of the peaks in the chromatograph.

Block 204, according to one or more embodiments, may include measuring the plurality of peak areas from a plurality of biomarkers in the sample of crude oil. For the purposes of the present disclosure, a biomarker is a specific carbon compound present in the mixture of carbon compounds in crude oil. The plurality of biomarkers may include biomarkers at carbon lengths of 6 carbons, 9 carbons, 17 carbons, 25 carbons, and combinations thereof.

At block 204, in accordance with one or more embodiments, measuring the peak area of a plurality of biomarkers includes measuring biomarkers at carbon lengths of 6, 9, 17, 25, and combinations thereof. Measuring the biomarkers may include identifying the peaks that correspond to the biomarkers during separation using the gas chromatography instrument 102 by selected ion monitoring. Identifying by selected ion monitoring may include identifying peaks at the m/z ratios corresponding to the carbon lengths of 6, 9, 17, 25, and combinations thereof. Once the peaks are identified, block 204 may include measuring the peak areas. Peak areas may be measured by any method known to those of ordinary skill in the art. One method of measuring peak areas is integrating the area under the curve of the peak. The m/z ratio may identify which peak areas correspond to a biomarker. The m/z ratio for a biomarker with a carbon length of 6 may include 26.0, 27.0, 28.0, 29.0, 32.0, 38.0, 39.0, 40.0, 41.0, 42.0, 43.0, 44.0, 51.0, 53.0, 55.0, 56.0, 57.0, 58.0, 69.0, 70.0, 71.0, 86.0, 87.0. and combinations thereof. The m/z ratio for a biomarker with a carbon length of 9 may include 27.0, 28.0, 29.0, 39.0, 40.0, 41.0, 42.0, 43.0, 44.0, 53.0, 55.0, 56.0, 57.0, 58.0, 69.0, 70.0, 71.0, 72.0, 84.0, 85.0, 86.0, 98.0, 99.0, 128.0, and combinations thereof. The m/z ratio for a biomarker with a carbon length of 17 may include 27.0, 29.0, 39.0, 41.0, 42.0, 43.0, 44.0, 54.0, 55.0, 56.0, 57.0, 58.0, 67.0, 68.0, 69.0, 70.0, 71.0, 72.0, 82.0, 83.0, 84.0, 85.0, 86.0, 97.0, 98.0, 99.0, 111.0, 112.0, 113.0, 126.0, 127.0, 140.0, 141.0, 154.0, 168.0, 169.0, 183.0, 197.0, 240.0, and combinations thereof. The m/z ratio for a biomarker with a carbon length of 25 may include 18.0, 27.0, 28.0, 29.0, 39.0, 41.0, 42.0, 43.0, 44.0, 54.0, 55.0, 56.0, 57.0, 58.0, 67.0, 68.0, 69.0, 70.0, 71.0, 72.0, 81.0, 82.0, 83.0, 84.0, 85.0, 86.0, 96.0, 97.0, 98.0. 99.0, 100.0, 110.0, 111.0, 112.0, 113.0, 114.0, 125.0, 126.0, 127.0, 128.0, 139.0, 140.0, 141.0, 142.0, 154.0, 155.0, 156.0, 168.0, 169.0, 170.0, 182.0, 183.0, 184.0, 196.0, 197.0, 198.0, 210.0, 211.0, 212.0, 224.0, 225.0, 226.0, 238.0, 239.0, 240.0, 252.0, 253.0, 254.0, 266.0, 267.0, 268.0, 280.0, 281.0, 282.0, 294.0, 295.0, 309.0, 323.0, 352.0, 353.0, 354.0, and combinations thereof. The cumulation of the m/z ratios for each biomarker results in a unique fragment pattern that may be used to identify the biomarker. Identifying the biomarker may occur by comparing the unique fragment pattern with a database, to literature, or through the prior knowledge of an experienced operator. It is known to those skilled in the art that databases are available to identify compounds using unique fragment patterns. The database may include the National Institute of Standards and Technology (NIST) Mass Spectral Library, the Wiley Registry of Mass Spectral Data, the Global Natural Products Social Molecular Networking (GNPS) database, and any known other commercial or open-source mass spectral database.

At block 206, method 200 includes determining a composite measurement from the plurality of peak areas, according to one or more embodiments. Determining the composite measurement may include a relationship between the peak areas of the plurality of biomarkers, as described in Equation 1 below.

$$x=\{C25/(C25+C6)\}/\{C17/(C17+C9)\} \quad \text{Equation 1}$$

In Equation 1, C25 may represent the peak area for the biomarker at a carbon length of 25. The carbon length of 25 may have a m/z ratio of about 353 g/mol. C6 may represent the peak area for the biomarker at a carbon length of 6. The carbon length of 6 may have a m/z ratio of about 80 g/mol. C17 may represent the peak area for the biomarker at a carbon length of C17. The carbon length of 17 may have a m/z ratio of about 240 g/mol. C9 may represent the peak area for the biomarker at a carbon length of 9. The carbon length of 9 may have a m/z ratio of about 128 g/mol. Calculations for determining the composite measurement may involve basic software programs, such as Excel, to complete.

In one or more embodiments, method 200 also includes the use of chemometrics. Chemometrics is a multidisciplinary field that uses statistical and mathematical methods to analyze chemical data. Properties, such as the WAT, may be predicted using one of the multiple ways of statistical and mathematical methods. One way may be to use principal component analysis (PCA) to reduce the dimensionality of the mass spectra data. PCA may make it easier to identify patterns in the data and to build predictive models. Another way to use chemometrics to predict properties based on mass spectra may be to use partial least squares (PLS) regression. PLS regression is a multivariate statistical method that may be used to predict a continuous response variable from a set of predictor variables. In the case of mass spectra, the predictor variables are the intensities of the different m/z ratios in the spectrum. The response variable is the property that is predicted, such as the concentration of a particular compound or the melting point of a material. Chemometrics may also be used to build classification models to predict categorical properties from mass spectra. For example, chemometrics may be used to build a model to predict whether a particular sample has a specific property or not based on its mass spectrum. The specific chemometric methods that may be used to predict properties based on mass spectra will depend on the specific problem that is being solved. However, chemometrics is a powerful tool that can be used to extract valuable information from mass spectra data.

At block 208, method 200 includes predicting a wax appearance temperature by a correlation with the composite measurement, according to one or more embodiments. Correlating the composite measurement to the WAT may include applying a linear equation. Determining the linear equation may include first graphing WAT measurements on a y-axis and composite measurements on an x-axis. Graphing may be done using basic software programs, such as Excel. Determining the linear equation may then include applying a linear least squares analysis to the graph. The linear least squares analysis may result in a linear equation. Determining the linear equation may require basic software programs, such as Excel. The linear least squares analysis may further result in a $R^2$ value, where the $R^2$ value relates to the strength of the linear equation. A $R^2$ value of 0.90 or greater may relate to a strong linear correlation. Correlating the composite measurement to the WAT may include applying the linear equation that results from the linear least squares analysis. Applying the linear equation may yield a WAT from the composite measurement for the sample of crude oil.

The graphing method used for graphing WAT measurements may include wax isolation to determine the wax content and analysis by differential scanning calorimetry (DSC) to identify the WAT. Wax isolation may include dissolving the crude oil sample in a series of suitable solvents such as heptane, acetone, and toluene. The choice and amount of solvent may depend on the source and the amount of the crude oil sample. The crude oil sample dissolved in the series of solvents may be subjected to evaporation to remove the final solvent. Evaporation of the final solvent may isolate the wax present in the crude oil sample. Once the wax is isolated, DSC may be used to determine the WAT.

Figure 3:
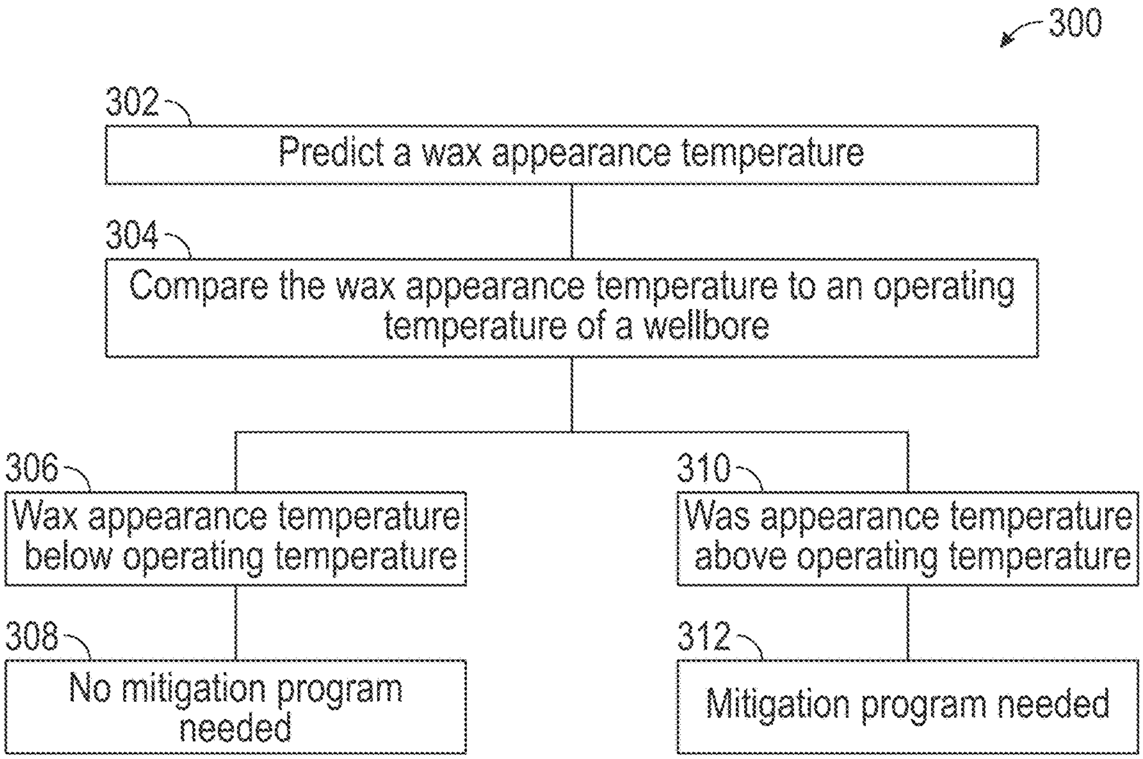
FIG. 3 is a flowchart of an operation, according to one or more embodiments.

In another aspect, embodiments disclosed herein relate to a wellbore operation where the wax appearance temperature is compared to an operating temperature to forecast a need for a mitigation program. A wellbore operation 300 according to one or more embodiments is depicted in FIG. 3. Initially, the wellbore operation 300 includes, at block 302, predicting a wax appearance temperature.

According to one or more embodiments, the wellbore operation 300 at block 302 may include predicting a WAT from a plurality of peak areas with a chromatography instrument 100 in a sample of crude oil from the wellbore. The plurality of peak areas may include a plurality of biomarkers. The plurality of biomarkers may include carbon molecules with a carbon length of 6, 9, 17, 25, and combinations thereof.

At block 304, the wellbore operation 300 includes comparing the wax appearance temperature to an operating temperature of a wellbore. The operating temperature of the wellbore may be determined by well logging. The operating temperature may also be determined by any suitable well measurement device. Comparing the WAT to the operating temperature of the wellbore may include the WAT being above the operating temperature, the WAT being below the operating temperature, or the WAT being equal to the operating temperature. The operating temperature may vary based on the wellbore, the weather, the geographical location, the depth at which the temperature is measured. By way of example and not limitation, the operating temperature may vary from a temperature of about 30 °C to a temperature of about 300 °C. If the temperature of the process, pipeline, wellbore is at or below WAT, wax precipitation may occur. This phenomenon can be used to anticipate wax formation or support corrective action.

According to one or more embodiments, block 306 of the wellbore operation 300 includes the WAT equaling a temperature below the operating temperature of the wellbore. Below refers to the WAT equaling a temperature that is less than the operating temperature. In the wellbore operation 300, if block 306 is true, the operation continues to block 308 where no mitigation program is needed. That is, the wax appearance tendency may be considered low when the WAT is below the operating temperature, as the wax will not form when the wellbore is operating at temperatures above the wax appearance temperature.

According to one or more embodiments, block 310 of the wellbore operation 300 includes the WAT equaling a temperature above the operating temperature of the wellbore. Above refers to the WAT equaling a temperature that is greater than the operating temperature. In the wellbore operation 300, if block 310 is true, the operation continues to block 312 where a mitigation program is needed. That is, the wax appearance tendency may be considered high when the WAT is above the operating temperature, as the wax will form when the wellbore is operating at temperature below the wax appearance temperature.

In accordance with one or more embodiments, block 312 of the wellbore operation 300 includes a mitigation program. The mitigation program may be a thermal treatment or a chemical treatment. The thermal treatment may include steam injection or any heating of the pipeline using any known electrical or mechanical process. The chemical treatment may include the addition into the wellbore of a suitable wax inhibitor or solvent to dissolve the wax, such as xylene or toluene. The chemical treatment may also include any thermochemical reaction that produces heat, i.e. an exothermic reaction.

Embodiments of the present disclosure may provide at least one of the following advantages. Advantages may be possible using a chromatography instrument as compared to current methods in the art. Methods using a chromatography instrument 100 may require a small volume of crude oil for analysis. As described in the present disclosure, volumes may be as small as about 0.5 mL or even lower, such as about 1 μL for methods using a chromatography instrument 100. Current methods in the art, which may include standard method UOP-46 and ASTM-2500, tend to require amounts of sample that vary based on the type of sample and the amount of wax in the sample. The amount of sample required tends to be at least as 5 grams. The density of crude oil may vary depending on the grade and may range from 0.700 to 0.950 g/cm$^3$. A density in this range would result in a sample volume over 0.5 mL. Thus, methods of the present disclosure may require less volume than the current methods in the art.

Additionally, methods using a chromatography instrument 100 may require less processing of the sample of crude oil than current methods in the art. Standard method UOP-46 tends to require specific steps to isolate the wax from the sample of crude oil. After the wax is isolated, another instrument, such as DSC, tends to be required to determine the WAT, as in standard method ASTM-2500. Methods of the present disclosure may require no additional processing. Methods of the present disclosure may include direct injection of the sample of crude oil with no other instruments required to determine the WAT.

Other advantages provided by embodiments of the present disclosure may include the following. Methods using a chromatography instrument 100 may require less time than current methods in the art. Current methods in the art may use standard method UOP-46 to isolate wax from a sample of crude oil. Once the wax is isolated, current methods in the art may then use standard method ASTM-2500 to determine the WAT via differential scanning calorimetry or cross polarization. These current methods in the art tend to require at least four days. Methods of the present disclosure may require less than two hours. Less time may be important in wellbore operations as it leads to a real time determination of the WAT. A real time determination of the WAT may lead to rapid determination of mitigation needs, which may correspond to preventing flow assurance problems and equipment damage.

Additionally, methods using a chromatography instrument 100 may need only one operator to complete the method. Current methods in the art, which may include UOP-46 and ASTM-2500, tend to require a minimum of two operators to complete. This is due to a lengthy method time and the use of solvents and cryogenics, which for safety reasons, require a minimum of two operators. Methods of the current disclosure may require less operators to complete.

Further advantages provided by the present disclosure may include the following. Methods using a chromatography instrument 100 may consume less solvent than current methods in the art. Current methods in the art tend to require up to 100 mL in solvents. The solvents may include hexane, acetone, toluene, liquid nitrogen, and combinations thereof. The present disclosure may consume only minor amounts of solvent, which may be needed to wash the chromatography syringes and clean any rinse vials used for the injection. Methods of the current disclosure may consume 99.9% less solvent than current methods in the art.

Additional advantages of the present disclosure may concern embodiments of the calculation of a wax appearance temperature. Methods using a chromatography instrument 100 may involve simple calculations to determine the WAT. These calculations may be carried out using basic software, such as Excel, to complete. Other examples of correlation software may be used, such as R or Eigenvector. Current methods in the art tend to require complex calculations and special software. Methods of the current disclosure may provide simple calculations to determine the WAT. The simple calculations may be used to track the WAT in real time and in an environmentally friendly manner.

EXAMPLES

A sample of crude oil was analyzed via a gas chromatography instrument with a mass spectroscopy instrument. The gas chromatography instrument was fitted with a non-polar chromatographic column (DB1, 60 m long, 0.25 mm ID and 2.5 um film thickness). The column was operated under a constant carrier gas (helium) flow of 1.0 mL/min. The gas chromatography oven was ramped from 180 °C to 300 °C at 5 °C/min. To ensure the reproducibility of the analysis, an auto sampler was installed on the gas chromatography instrument. The sample of crude oil was analyzed by a mass spectroscopy instrument after the components were separated by the gas chromatography instrument.

Figure 4:
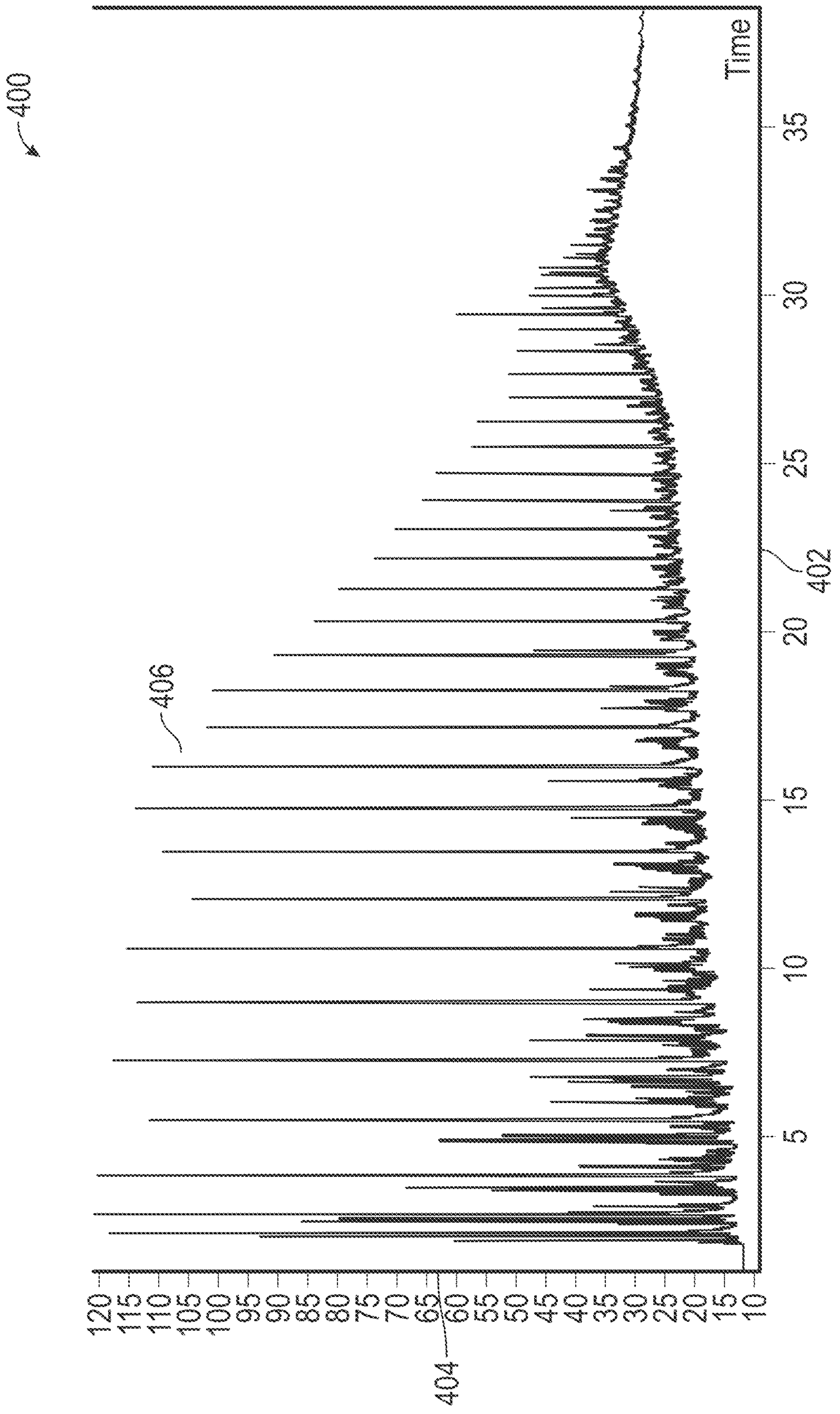
FIG. 4 is an example total ion chromatograph, according to one or more embodiments.

FIG. 4 is an example chromatograph of a sample of crude oil, separated using a gas chromatography instrument. A total ion chromatograph 400 is depicted. The total ion chromatograph 400 includes an x-axis 402. The x-axis 402 may include retention times. The total ion chromatograph includes a y-axis 404. The y-axis 404 may include total ion currents. The total ion chromatograph further includes a plurality of peaks 406.

Figure 5:
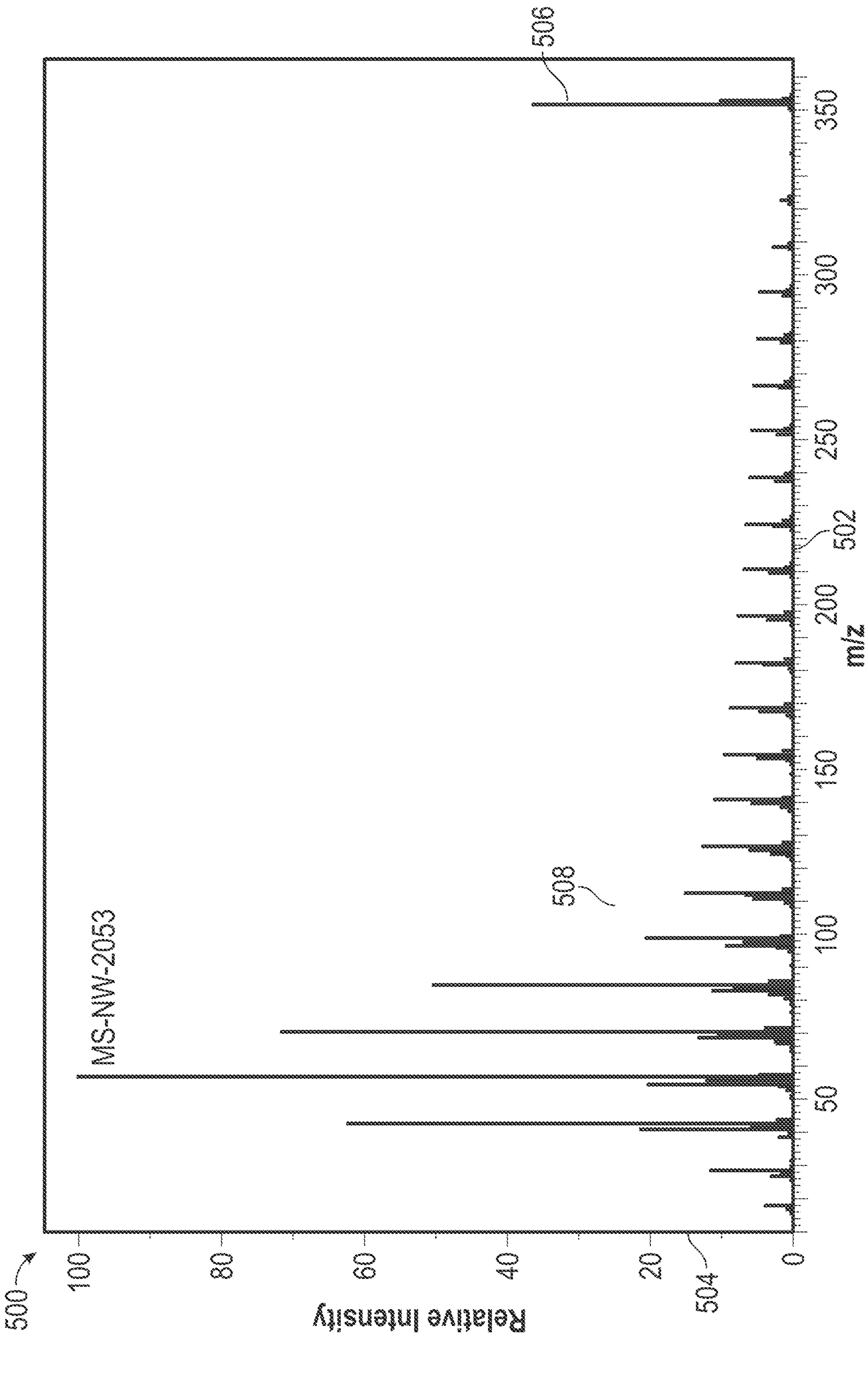
FIG. 5 is an example mass spectroscopy pattern, according to one or more embodiments.

FIG. 5 is an example mass spectroscopy instrument fragment pattern. FIG. 5 shows the mass spectroscopy instrument fragment pattern 500 for the C25 biomarker pentacosane. The mass spectroscopy instrument fragment pattern 500 includes an x-axis 502. The x-axis 502 may include m/z ratios. The mass spectroscopy instrument fragment pattern 500 includes a y-axis 504. The y-axis may include relative intensity amounts. The mass spectroscopy instrument fragment pattern 500 further includes a molecular ion peak 506 and a plurality of fragment peaks 508.

Figure 6:
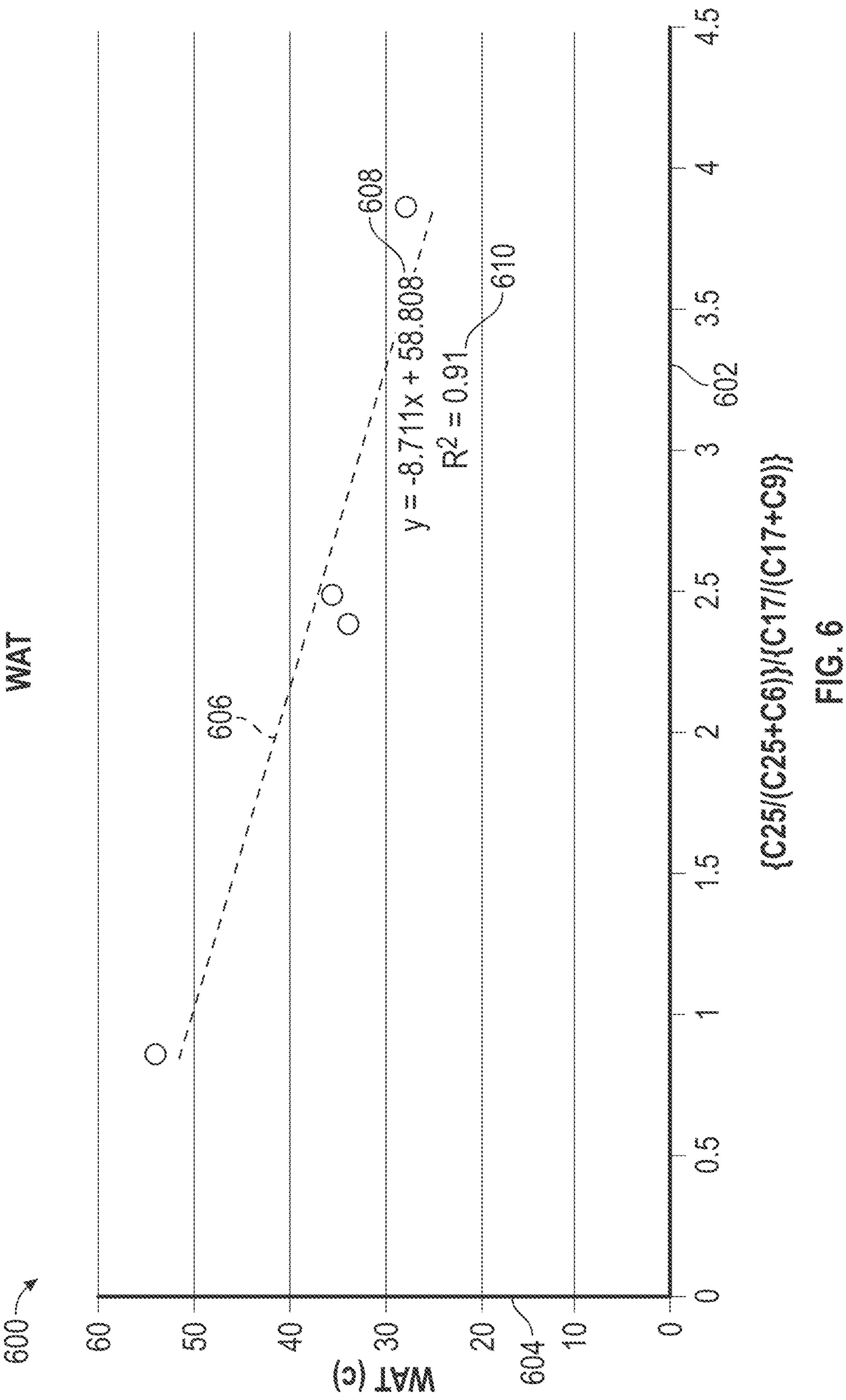
FIG. 6 is an example graph of a linear correlation, according to one or more embodiments.

FIG. 6 is an example graph of a linear correlation between a composite measurement and a wax appearance temperature, according to one or more embodiments. The graph 600 includes an x-axis 602. The x-axis 602 may include a range of composite measurements. The graph 600 includes a y-axis 604. The y-axis 604 may include a range of wax appearance temperatures. The range of wax appearance temperatures may be determined by a method further described below. The graph 600 includes a linear least squares analysis 606. The linear least squares analysis 606 may produce a linear equation 608 and a $R^2$ value 610. The linear equation 608 may correlate a composite measurement of a sample of crude oil to a wax appearance temperature, where inputting a new composite measurement as the x value will calculate a new wax appearance temperature as the y value. The $R^2$ value 610 may indicate the strength of the correlation, where a strong correlation may exist at any value greater than 0.90.

The method of determining the range of wax appearance temperatures for y-axis 604 was conducted as follows. The wax isolation was carried out to determine the wax content and analyze it by differential scanning calorimetry (DSC) to identify the WAT. The sample was a hydrocarbon, so the deasphalting step was accomplished by adding excessive heptane or pentane and then filtering. First, the sample was mixed with pentane (35 mL) and stirred thoroughly to insure full solubility. Then, the solution was mixed with acetone (110 mL) and stirred thoroughly and placed in a cold bath at −20 °C to −30 °C to aid the wax precipitation. The sample was filtered through a cold filtration setup and washed three times with cold acetone-pentane (3:1 ratio) mixture until a clear eluent was observed. After the filtration, hot toluene was used to collect the wax crystals into a new flask. The toluene was evaporated and the unpurified wax crystals were subjected to purification using alumina or silica packed column chromatography and hexane for elution to produce pure wax. The pure wax was free from interferences, particularly aromatic compounds. After the purification, the hexane was evaporated using nitrogen gas purging. The exact mass of the purified wax was weighted and reported as a percentage of the sample. The sample was analyzed by DSC to measure the wax appearance temperature.

The WAT was determined using NETZSCH differential scanning calorimetry (DSC 204 F1) coupled with refrigerated cooling system. Scans were run at a heating rate of 5 °C/min under nitrogen purge at a rate of 20 $cm^3$/min between room temperature (RT) to 100 °C range. The operating parameters for WAT are illustrated in Table 1.

TABLE 1

| | DSC conditions for determination of wax appearance temperature (WAT). |
|---|---|
| Instrument | (DSC 204 F1) NETZSCH |
| Purging gas | Nitrogen or helium, constant flow mode, 20 mL/min |
| Temperature program | Temperature program: The sample is cooled to −20 °C then heated to 100 °C @ 5 °C/min (hold 5 minutes) and then cooled to −20 °C (hold 5 minutes) @ 5 °C/min. Finally, the sample is heated to 100 °C @ 5 °C/min. |
| Sample mass | 5-20 mg |
| Analysis time | 40 min |

Figure 7:
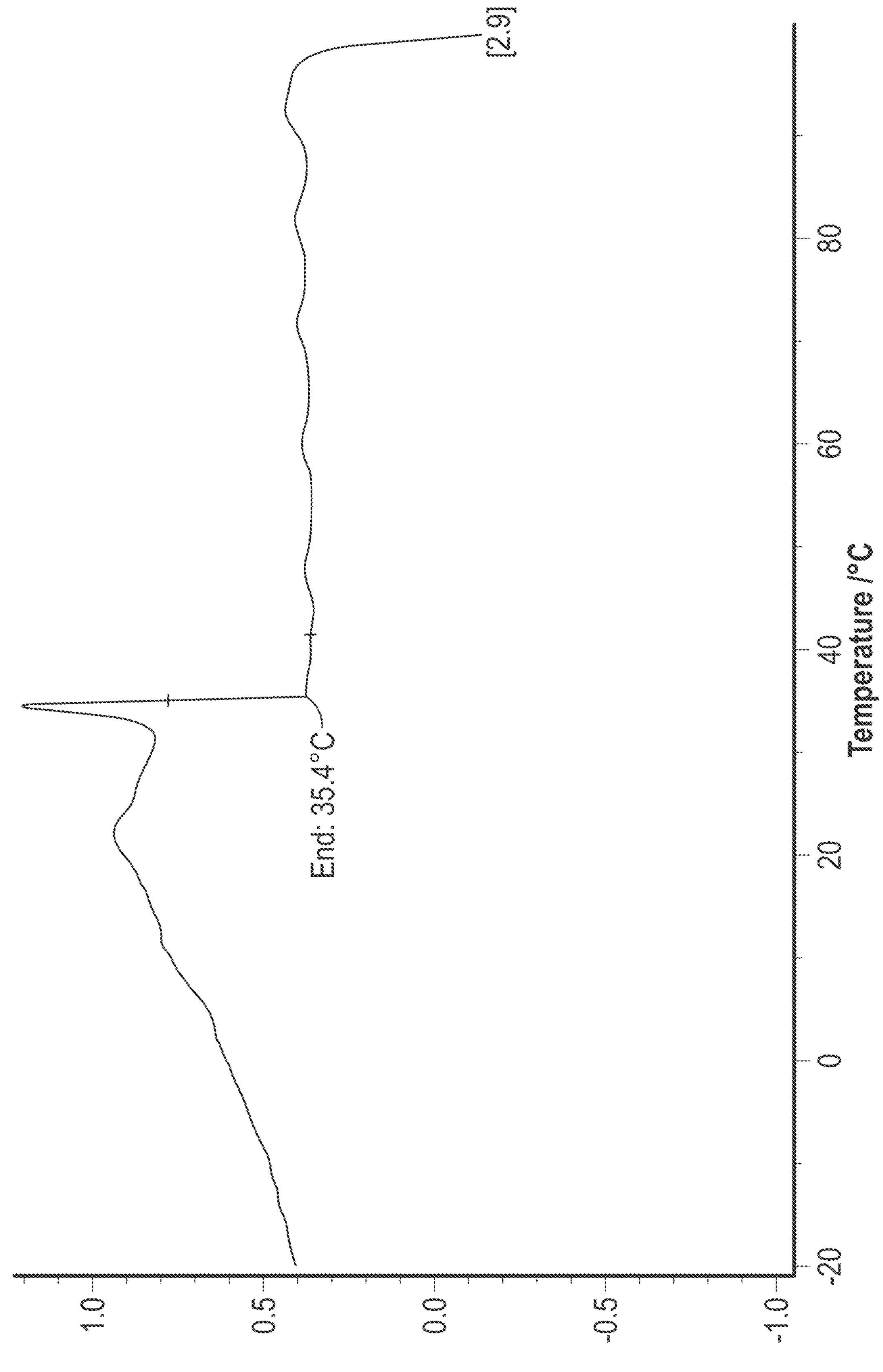
FIG. 7 is an example differential scanning calorimetry thermogram, according to one or more embodiments.

DSC was used to determine the wax appearance temperature (WAT). FIG. 7 is an example DSC thermogram, according to one or more embodiments. As shown in FIG. 7, the sample's WAT was determined as 35.4 °C. WAT is determined as the temperature at which the first wax crystal appears upon cooling the sample.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A method to predict a wax appearance temperature of crude oil comprising:
- injecting a sample of crude oil into a gas chromatography-mass spectroscopy instrument;
- measuring a plurality of peak areas using the gas chromatography-mass spectroscopy instrument;
- determining a composite measurement from the plurality of peak areas; and
- determining the wax appearance temperature from the composite measurement using a direct correlation of the composite measurement with the wax appearance temperature, wherein the direct correlation is a linear correlation with a $R^2$ value of 0.90 or greater.

2. The method of claim 1, wherein injecting the sample of crude oil occurs without dilution.

3. The method of claim 1, wherein the plurality of peak areas is measured from a plurality of biomarkers.

4. The method of claim 3, wherein the plurality of biomarkers comprises a biomarker at a carbon length of 6, a biomarker at a carbon length of 9, a biomarker at a carbon length of 17, and a biomarker at a carbon length of 25.

5. The method of claim 4, wherein the biomarker at the carbon length of 6, the biomarker at the carbon length of 9, the biomarker at a carbon length of 17, and the biomarker at a carbon length of 25 are each identified by a fragmentation pattern.

6. The method of claim 5, wherein the composite measurement x is given by x={C25/(C25+C6)}/{C17/(C17+C9)}, where CN is the peak area for the biomarker at carbon length of N, where N is 6, 9, 17, or 25.

7. The method of claim 3, comprising operating the chromatography instrument in selected ion monitoring mode to isolate mass-to-charge ratios (m/z) for the plurality of biomarkers.

8. The method of claim 7, wherein the mass-to-charge ratio (m/z) for the plurality of biomarkers comprises:
- a carbon length of 6 at 80 m/z;
- a carbon length of 9 at 128 m/z;
- a carbon length of 17 at 240 m/z; and
- a carbon length of 25 at 353 m/z.

9. A wellbore operation comprising:
- determining a wax appearance temperature, wherein determining the wax appearance temperature comprises:
  - injecting a sample of crude oil into a gas chromatography-mass spectroscopy instrument;
  - measuring a plurality of peak areas using the gas chromatography-mass spectroscopy instrument;
  - determining a composite measurement from the plurality of peak areas; and
  - determining the wax appearance temperature from the composite measurement using a direct correlation of the composite measurement with the wax appearance temperature, wherein the direct correlation is a linear correlation with a $R^2$ value of 0.90 or greater;
- comparing the wax appearance temperature to an operating temperature of the wellbore; and
- forecasting a need for a mitigation program.

10. The wellbore operation of claim 9, wherein the plurality of peak areas is measured from a plurality of biomarkers.

11. The wellbore operation of claim 10, wherein the plurality of biomarkers comprises a biomarker at a carbon length of 6, a biomarker at a carbon length of 9, a biomarker at a carbon length of 17, and a biomarker at a carbon length of 25.

12. The wellbore operation of claim 11, wherein the biomarker at the carbon length of 6, the biomarker at the carbon length of 9, the biomarker at a carbon length of 17, and the biomarker at a carbon length of 25 are each identified by a fragmentation pattern.

13. The wellbore operation of claim 9, wherein comparing the operating temperature is when the wax appearance temperature is either above or below the operating temperature of the wellbore.

14. The wellbore operation of claim 9, wherein the mitigation program is needed when the wax appearance temperature is equal to or greater than the operating temperature.

15. The wellbore operation of claim 9, wherein the mitigation program is a thermal or chemical treatment.

* * * * *